United States Patent [19]

Bailey

[11] Patent Number: 5,674,175
[45] Date of Patent: Oct. 7, 1997

[54] POINT-OF-USE INFECTIOUS WASTE DISPOSAL SYSTEM

[76] Inventor: John R. Bailey, P.O. Box 6315, Bluefield, W. Va. 24701

[21] Appl. No.: 594,810

[22] Filed: Jan. 31, 1996

[51] Int. Cl.$^6$ .............................. B09B 1/00; B65D 85/24
[52] U.S. Cl. ...................... 588/255; 206/366; 588/258; 588/259
[58] Field of Search .................... 405/128; 588/249, 588/252, 255, 258, 259, 901; 206/364, 365, 366

[56] References Cited

U.S. PATENT DOCUMENTS

| | | | |
|---|---|---|---|
| 3,782,299 | 1/1974 | Egger | 588/255 |
| 4,717,510 | 1/1988 | James | 588/255 |
| 4,816,307 | 3/1989 | Honeycutt | 206/366 X |
| 4,900,500 | 2/1990 | Honeycutt | 206/366 X |
| 5,046,613 | 9/1991 | Baudry et al. | 588/258 X |
| 5,236,088 | 8/1993 | Dhority et al. | 588/258 X |
| 5,245,117 | 9/1993 | Withers et al. | 588/249 |
| 5,322,603 | 6/1994 | Kameda et al. | 588/255 X |
| 5,383,862 | 1/1995 | Berndt et al. | 206/365 |
| 5,434,338 | 7/1995 | Williams et al. | 588/255 |

OTHER PUBLICATIONS

*Hawley's Condensed Chemical Dictionary*, 12th Edition, Van Nostrand Reinhold Company, New York, 1993, pp. 942, 943.

*Primary Examiner*—George A. Suchfield
*Attorney, Agent, or Firm*—Parkhurst, Wendel & Burr, L.L.P.

[57] ABSTRACT

A method for containing potentially infectious devices. The potentially infectious devices are deposited is a container to which is added an MDI-based urethane prepolymer-containing composition to at least partially envelope the potentially infectious devices. The prepolymer containing composition is caused to harden through polymerization to immobilize the devices, and to act as a sterilizing or disinfectant agent due in large part to the exothermic nature of the reaction.

6 Claims, No Drawings

POINT-OF-USE INFECTIOUS WASTE DISPOSAL SYSTEM

TECHNICAL FIELD OF THE INVENTION

The present invention relates to infectious waste disposal systems and particularly those systems designed for use in hospitals and other environments wherein medical practitioners routinely contaminate a host of devices such as needles, syringes, tubing, and scalpels with blood and other bodily fluids that then require disposal.

BACKGROUND OF THE INVENTION

In hospitals, clinics, and other environments wherein ill patients are routinely examined and treated, medical practitioners contaminate a host of devices such as needles, syringes, tubing, and scalpels with blood and other bodily fluids. Such contamination is often done when feeding patients, drawing blood, vaccinating, and otherwise inoculating patients against various diseases. Quite often, patients' bodily fluids are infected with pathogenic bacteria, viruses, fungi, and other matter. The potential source of pathogenicity has been acute due to the presence of certain pathogens such as hepatitis B and the AIDS virus, among other deadly and infectious materials.

These pathogenetic materials are potentially a source of infection for doctors, nurses, aids, orderlies, technicians, and even to visitors to the hospital or clinic, as well as to the patients themselves. The infected devices must thus be contained and/or destroyed.

Currently, infectious waste, called "sharps", is generally disposed of by insertion of the infected material into a passive hard plastic container. These containers are then removed by housekeeping personnel and sent to a site for bagging and storage. After bagging, the containers are often stored or removed to yet another site for sterilization. Even when closed, locked, and bagged, the containers are not airtight, and thus can potentially spill and contaminate the atmosphere. During handling of the waste containers infected needles often penetrate storage containers, thus providing a potentially dangerous condition for housekeeping personnel.

Following sterilization, the contaminated material is often removed to another location for incineration, storage, or disposal in a landfill. Thereafter, the waste disposal containers resemble, and are often referred to, as "porcupines" because the often-used plastic containers shrink around the needles and other devices when heated in an autoclave or similar device, resulting in needle exposure through the sidewalls of the containers. In this condition, the containers are indeed quite dangerous to handle, whether or not they remain to house the infectious devices.

In addition to the above recited difficulties, current state of the art disposal techniques are further flawed in the use of so-called "anti-removal" or "anti-theft" containers. Infectious devices are often put into plastic containers that contain guards for preventing needle retrieval. However, it is relatively easy to reach into such containers and retrieve the "sharps." As such, current disposal methods do not render the needles and sharps irretrievable and unstable at the point of disposal.

One of the most serious deficiencies with current disposal methods is that they do not prevent the aerosoling or spilling of infectious materials into the ambient atmosphere, thus potentially causing the spread of infectious germs, bacteria, fungi, and vital fragments. Current containers are not airtight, even when they are eventually closed and locked. As such, there remains an outstanding potential for cross-infection by vectors such as flies, rodents, etc., and "odor" is, of course, a big problem.

It is thus an object of the present invention to provide a superior means for containing potential infectious devices that overcomes the difficulties recited above.

This and further objects of the present invention will be more fully appreciated when considering the following disclosure.

SUMMARY OF THE INVENTION

In its broadest sense, the present invention relates to a method for sterilizing and containing potentially infectious devices. The method comprises depositing the potentially infectious devices in a container to which is added a sufficient quantity of a particular urethane prepolymer-containing composition. The composition is to be added to a container to fully or at least partially envelope the potentially infectious devices. The urethane prepolymer-containing composition is then hardened with a corresponding exotherm to immobilize and sterilize or at least neutralize the potentially infectious devices.

Although there is general reference in U.S. Pat. No. 4,900,500 to use a reaction product of a polyol and a diisocyanate to encapsulate and cover "sharps," the patent gives no information about the type of polyol and/or diisocyanate to be used. The composition used in applicant's invention and described in detail below gives a product that is biocompatible, hydrophobic, and has good characteristics from a leaching point.

DETAILED DESCRIPTION OF THE INVENTION

The present method involves the entrapment, anchoring and fuming or precipitation of contaminated and/or infected "sharps" and their aerosol through the use of a container and solidifying agent at the point of disposal. The container is first filled by hospital personnel with the infected "sharps" material, and then filled with a liquid which turns into a solid block of plastic with associated fuming and surface coating within a short period after the liquid is poured over the "sharps" or infections devices. The liquid and fume contains biocides and produces biocidal activity and sanitizing heat during the course of the reaction, which is decidedly exothermic. The preferred solidifying liquid is a urethane prepolymer based on 4,4'-diphenylmethane diisocyanate (MDI) (a mixture of various isomers thereof) having polyether linkages (based on polypropylene glycol). A ricinoleic acid (castor oil) component is added to the prepolymer to form a polyurethane. The urethane prepolymer and castor oil-containing composition incorporates the potentially infectious fluids into their polymer matrices as the polymerization proceeds. It is hypothesized that the composition reacts through a polymerization cascade and causes a grafting reaction to take place whereby the organic matter in the infectious waste is thereby "caught up", bound or covalently reacted with the prepolymer and thus becomes a part of the "thermoset" matrix.

The MDI component may be used in its monomeric form or as an isomeric mix of the 2,4' and 4,4' isomers. Polymeric or oligomeric MDI may be used also as well as polymethylene polyphenyl isocyanate (either the 2,4'- or 4,4'- isomers or mixtures thereof). The term "MDI-based" in the claims is intended to include each of these embodiments.

The polypropylene glycol providers of the polyether linkages in the MDI-based urethane-containing prepolymer include both propylene glycol and polypropylene glycol. The polypropylene glycol may be up to any molecular weight that does not interfere with the proper mixing of the components as described herein.

The urethane prepolymer-containing composition is stored hermetically away from moisture and air before being used to engulf and encapsulate the "sharps." Subsequently, in the presence of a catalyst such as alkyl tin or mercury compounds or tertiary amines, for example, when water vapor or a liquid water is added to the oligomer, part of the excess isocyanate groups are converted to primary amines with the concurrent evolution of carbon dioxide. The primary amines thus produced then react with other isocyanate linkages to form crosslinks and a solid mass.

When using urethane prepolymers, promoters are not necessary as ambient moisture combined with catalysts that are generally included with the prepolmers are all that is necessary to start the cross-linking or "hardening" reactions. The prepolymer, of course, must be kept away from moisture as it begins to harden on contact with moisture vapor.

Also included as possible preferred expedients in the system are aldehydes such as formaldehyde and glutaraldehyde and phenol and its derivatives such as orthophenylphenol and its sodium salt as sterilants and/or disinfectants.

While an "oil" based or hydrophobic system is satisfactory, a more preferred system is one that is aqueous based. The aqueous based systems are preferred for land-fill considerations as aqueous based materials are easier to contain in a land-fill area due to various legal restrictions on burying "organic" materials.

The preferred viscosity of the present composition is that of water, approximately between 0 and 1000 cps when measured on a Brookfield viscometer at 20 rpms with a number 4 spindle. Although the composition can be thixotropic in nature, it is preferable not to employ a highly viscous material so that the urethane prepolymer-containing composition has the desirable "penetrating" effect to insure complete coverage over all utensils found within the container. If viscosity is to be increased, viscosity enhancers such as CABOSIL® PTG, which is a hydrophobic fumed silica treated with polydimethylsiloxane, may be employed. One can also employ PMMA, PECA and PEMA, as well as cellulose esters or polycarboxylic or polyacrylic acids for water based systems.

It is further contemplated that, in practicing the present invention, an initiating agent or catalyst be employed to promote the polymerization of the urethane prepolymer. Preferably, the catalyst consists of a persulfate, peroxide, or perborate, alone, or in a solvent or plasticizer such as a detergent, soap, or surfactant.

Catalysts can be deposited on the inside of the container or in a paper or sponge material which can be placed in the container to provide a concentration from approximately 0.001% to 5% of the effective volume of the container. A suitable solvent for the initiating agent can be water, while diocylphthalate can be employed as a suitable plasticizer, or in the case of ammonium persulfate or sodium perborate tetrahydrate, it may be used as a dry powder.

A urethane prepolymer based on MDI, polypropylene glycols, and a ricinoleic acid component is described in U.S. Pat. No. 4,285,854, hereby incorporated by reference. The patent describes an elastomer useful as a tire-filling composition; the prepolymer does include the components used in applicant's invention.

When the components are being mixed to from a composition that will ultimately harden and encapsulate the "sharps," normally about 50 to about 80 weight percent ricinoleic acid will be mixed with about 20 to about 50 weight percent of a polyurethane prepolymer based on MDI and polypropylene glycols. The preferred mixtures contain about 60 to about 75 weight percent of ricinoleic acid and about 25 to about 40 weight percent of the prepolymer. The most preferred mixture contains about 65 weight percent ricinoleic acid and about 35 weight percent polyproplyene glycol and MDI-based polyurethane propolymer.

The two components are mixed at room temperature for about 1 to about 3 minutes and the resulting composition is poured over the "sharps" and allowed to set for about 15 minutes.

EXAMPLE I

A 2 liter container that has been blow molded from high density polyethylene is fitted with a screw lid. The container is filled with syringes and needles of the type used for intramuscular injection and venous blood withdrawal. After the container is filled with the syringes, there is sufficient void space for introduction of the immobilizing liquid to intermingle and fill the container. As such, the container is then filled to the bottle shoulder level with the solidifying composition containing an MDI-based urethane prepolymer with polyether linkages and a ricinoleic acid component.

The container is then closed. The container is allowed to sit for a period of time to give the solidifying liquid an opportunity to polymerize. As the reaction proceeds, heat is released from the exothermic reaction, causing a rise in temperature of the container and its contents to the range of approximately 150° to 200° F. As this occurs, a hard dense block of polyurethane forms in the container which completely locks and anchors the infected syringes, and prevents their retrieval and/or use. Further, the heat of polymerization sanitizes the container and forms a surface film in the voids. As the container begins to cool down, it can be handled as ordinary sanitary trash.

I claim:

1. In a method for containing potentially infectious devices comprising depositing the potentially infectious devices in a container, the improvement comprising adding to said container a sufficient quantity of a hardenable compassion to at least partially envelop said potentially infectious devices, said hardenable composition comprising an MDI-based urethane containing prepolymer-containing liquid capable of polymerizing in an exothermic reaction to immobilize said potentially infectious devices, said prepolymer containing a ricinoleic acid component.

2. The method of claim 1 wherein the MDI-based urethane prepolymer contains polyether linkages.

3. The method of claim 2 wherein the polyether linkages are provided by polypropylene glycol.

4. The method of claim 1 wherein the MDI-based urethane propolymer contains polyether linkages provided by polypropylene glycol.

5. The method of claim 4 wherein the ricinoleic acid component is present in an amount of about 65 percent weight percent.

6. The method of claim 4 wherein the MDI-based urethane prepolymer containing polypropylene glycol-provided polyether linkages is present in an amount of about 35 weight percent.

* * * * *